United States Patent [19]

Hütsch et al.

[11] Patent Number: 4,946,278
[45] Date of Patent: Aug. 7, 1990

[54] GRAPHITE TUBE FURNACE WITH SPECIMEN SUPPORT FOR ATOMIC ABSORPTION SPECTROSCOPY

[75] Inventors: Bruno Hütsch; Bernd Schmidt, both of Bonn, Fed. Rep. of Germany

[73] Assignee: Ringsdorff-Werke GmbH, Bonn, Fed. Rep. of Germany

[21] Appl. No.: 373,174

[22] Filed: Jun. 28, 1989

[30] Foreign Application Priority Data

Jul. 9, 1988 [DE] Fed. Rep. of Germany ....... 3823346

[51] Int. Cl.⁵ .......................................... G01N 21/74
[52] U.S. Cl. .................................................... 356/312
[58] Field of Search ................................ 356/312, 244

[56] References Cited

U.S. PATENT DOCUMENTS 4,303,339  12/1981  Gläser et al. ......................... 356/312

FOREIGN PATENT DOCUMENTS 2924123  12/1980  Fed. Rep. of Germany .
3545635   6/1987  Fed. Rep. of Germany .
3722379   3/1988  Fed. Rep. of Germany .
2152234   7/1985  United Kingdom ................ 356/312

OTHER PUBLICATIONS

Journal of Analytical Atomic Spectroscometry, Mar. 1987, vol. 2, Ian Shuttler et al.: "Between–batch Variability of Thermal Characteristics of Commercially Available L/vov Platform Graphite Tube Atomisers and Analytical Accurary in Electrothermal Atomization, " etc.

Fresenius Z. Anal Chem (1986) 323: pp. 748–753; Heinz Falk et al.: "Spatially and temporally resolved temperature profiles in graphite furnaces."

*Primary Examiner*—F. L. Evans
*Attorney, Agent, or Firm*—Herbert L. Lerner; Laurence A. Greenberg

[57] ABSTRACT

A graphite tube furnace with a specimen support for use in atomic absorption spectroscopy has preferably knife-edged shaped flanges on the inner wall surface of the tube furnace. The specimen support is held on the flanges at a distance from the inner wall surface. This avoids the production of heat in the specimen support and heat flow from the tube furnace to the specimen support.

6 Claims, 3 Drawing Sheets

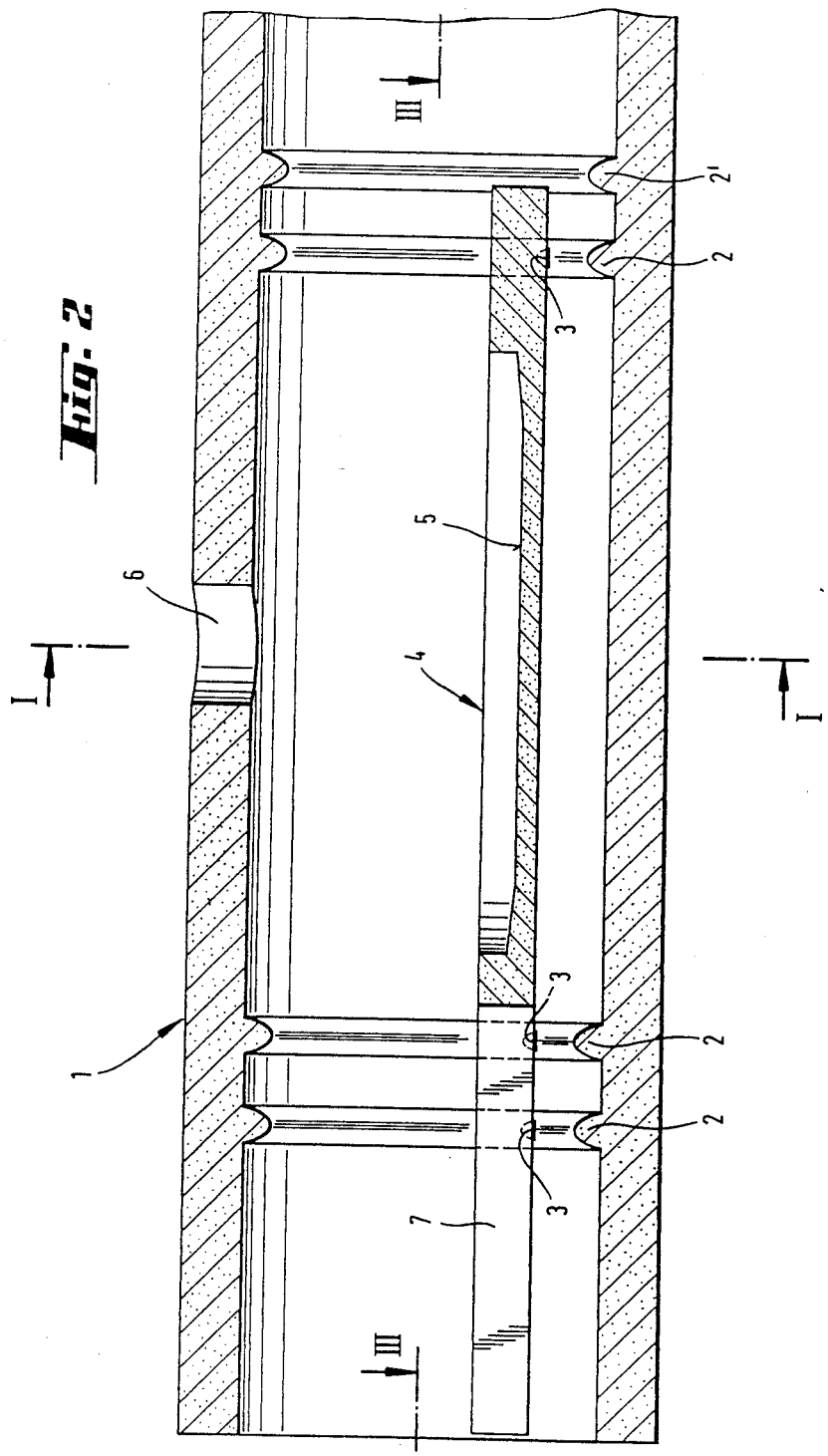

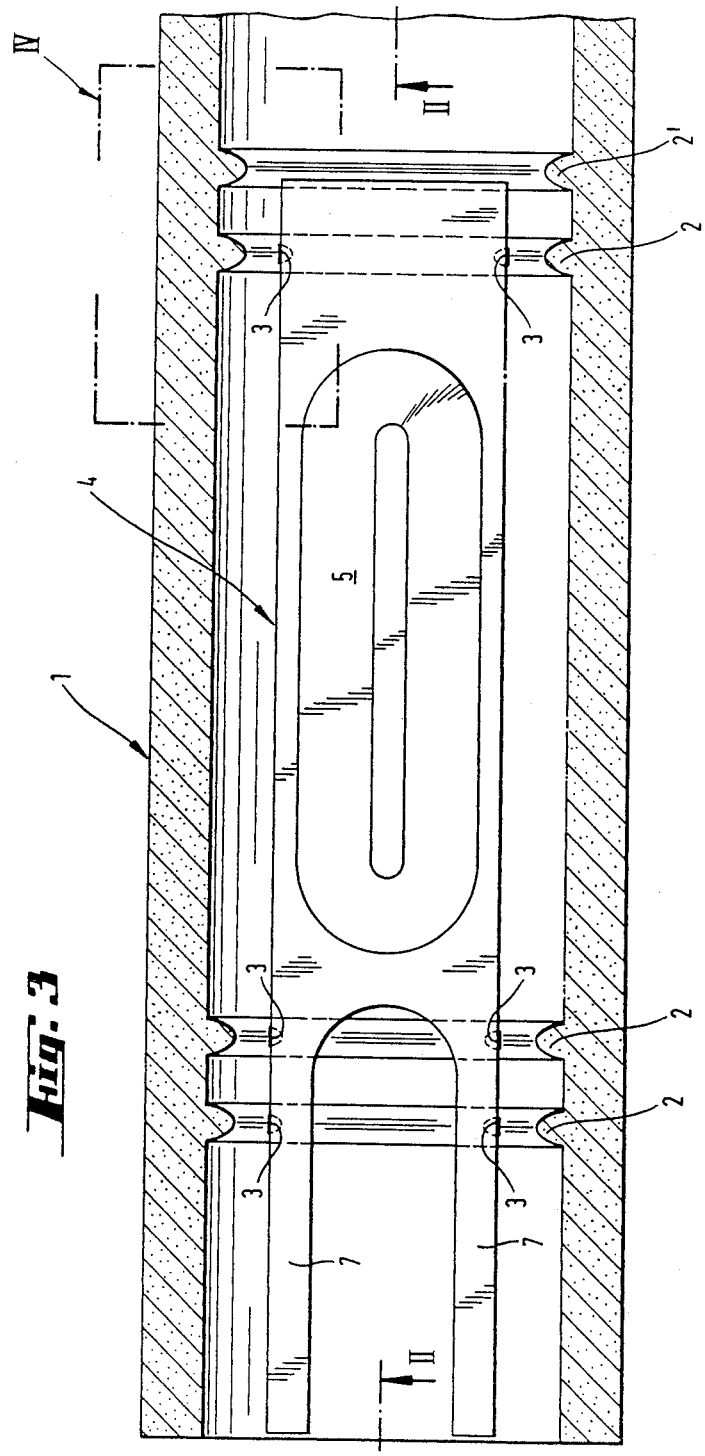

GRAPHITE TUBE FURNACE WITH SPECIMEN SUPPORT FOR ATOMIC ABSORPTION SPECTROSCOPY

The invention relates to a graphite tube furnace with a specimen support disposed in the furnace for atomic absorption spectroscopy.

In flameless atomic absorption spectroscopy (AAS), graphite tube furnaces which are heated to the necessary temperature by direct resistance heating are used for vaporization and atomizing of the specimen substance. The specimen is applied directly through an opening in the tube wall directly onto the wall surface of the tube furnace or is introduced through the ends of the tube furnace with the assistance of a specimen support, which is also known as a platform, that is provided with a small recess for receiving the specimen. As a result of the use of special specimen supports, the position of the specimen can be localized exactly and errors resulting from possible temperature gradients along the tube axis are largely avoided. On the other hand, it has been found that the heating rate of the specimen support which is also formed of graphite is essentially changed by contact between tube wall and the specimen support, since one part of the flow of heat flows through the specimen support, as discussed in the article "Spatially and Temporally Resolved Temperature Profiles in Graphite Furnaces", Fresenius Z. Anal Chem (1986) 323 pages 748–753. The effect of different heating rates and temperature differences between the tube and the specimen support has been investigated by I. L. Shuttler and H. T. Delves for the example of a measurement of small lead contents in blood, in The Journal of Analytical Atomic Spectroscopy, March 1987, Vol. 2, page 171. Above all, they found large differences in the time lag of the signal and the integral absorption and there was such a large variation in the measurement values that the method was not suitable for this purpose. A solution to the problem is expected in specimen supports which are heated exclusively by irradiation and not by Joules heat, wherein no bodily contact is made with the graphite tube furnace and the sample is held in a reproducible position in the graphite tube.

Essentially, three configurations of specimen supports have become known, which are distinguished by comparatively small contact surfaces between the specimen support and the tube wall and which significantly restrict electrical conduction and heat conduction between the wall and the support. Typical of the first group is the configuration according to German Published, Non-Prosecuted Application DE-OS No. 29 24 123, corresponding to U.S. Pat. No. 4,303,339. The specimen support therein has a trapezoidal cross-section and the edges of the wider side are engaged in flat dovetail-shaped channels milled in the tube wall. In the second configuration, the specimen support is provided with a lug which has a small cross-sectional area, is inserted in a bore in the graphite tube and the specimen support is held at a distance from the tube wall, as in German Published, Non-Prosecuted Application DE-OS No. 35 45 635 A1. Typical of the third group is a specimen support with a widened end section which is engaged in slots that extend from one end of the graphite tube. The specimen supporting part of the support is held in such a way as to extend freely at a distance from the tube wall, as in German Published, Non-Prosecuted Application DE-OS No. 37 22 379 A1.

All of the above-described structures reduce the flow of heat between the graphite tube and the specimen support and reduce the production of heat in the specimen support, thus permitting the precise location of the specimen support relative to the graphite tube and the reduction of a large part the further disadvantages above described. However, when rapid heating of configurations of the first and third types takes place repeatedly, damage occurs which greatly restricts the use of the graphite tubes. Fine cracks emanate from the grooves or slots which serve to guide and fix the specimen supports, the cracks giving rise to rupturing of the graphite tube after heating many times. Non-identical thermal coefficients of expansion of the specimen support and the tube impose additional pressure stresses upon heating, which can lead to tearing off of the slotted section. Breakdowns as a result of arcing are frequent if the mechanical stresses are restricted by a larger clearance. In such a case, there are also undesired vibrations at proximity to magnetic fields. Graphite tubes provided with grooves can also only be used in combination with the specimen support, since a specimen substance supplied directly to the wall surface collects in the grooves and is distributed over the entire wall surface. With configurations of the second type, the production cost of specimen support with turned plugs is very large, due to the small amount and brittleness of the graphite material. In fact, only vitreous carbon is suitable for specimen supports of that type, because of its high strength.

It is accordingly an object of the invention to provide a graphite tube furnace with a specimen support for atomic absorption spectroscopy, which overcomes the hereinafore-mentioned disadvantages of the heretofore-known devices of this general type and which does so in such a way that the specimen supports are held at a distance from the tube surface, the strength of the tube furnace is not influenced by grooves or slots and the production of the specimen supports is simple. Another object of the invention is the equalization of the temperature profile within the graphite tube furnace.

With the foregoing and other objects in view there is provided, in accordance with the invention, a graphite tube furnace assembly, comprising a graphite tube furnace having an inner wall surface, at least two peripheral flanges disposed on the inner wall surface, and a specimen support for atomic absorption spectroscopy supported on the flanges in the graphite tube furnace at a distance from the inner wall surface.

In accordance with another feature of the invention, the flanges are wedge-shaped and preferably in the shape of knife edges, for reduction of the contact surfaces.

In accordance with a further feature of the invention, the knife edges have a base width of substantially between 0.5 and 1.0 mm.

During the production of the tube furnace provided with flanges, graphite cylinders are bored out and worked out by backing off or recessing the flanges which are advantageously symmetrically disposed in the tube, that is they are spaced at equal distances as a pair from both end surfaces of the tube.

In accordance with an added feature of the invention, there is provided a pyrocarbon coating disposed on the inner wall surface of the graphite tube furnace. The abrasive resistance of the flanges, which in general is comparatively small, is matched to known stress requirements, as a result of the coating of the wall surfaces of the tube surface with pyrocarbon, which is known and usual, so that the flanges are not damaged by operation of the furnace.

In accordance with an additional feature of the invention, the flanges have slot-shaped recesses formed therein for guiding the specimen support. The positioning of the specimen support is established reproducibly by the slot-shaped recesses in the flanges which are advantageously produced by reaming or high frequency chiselling and the positioning is fixed by means of a buffer.

In accordance with a concomitant feature of the invention, one of the flanges is free of recesses and limits lengthwise movements of the specimen support like a buffer. The flange serving as a buffer is adjacent one end surface of the tube furnace.

The slotting of the graphite tube is limited exclusively to the flanges or webs and does not extend over the entire length of the tube as in a previously known construction, so that the probability of the formation of critical cracks destroying the tube must already be very much less for geometric reasons. In fact, hair-line cracks extending from the slots end in the roots of the flange and do not affect the operating life of the tube furnace. Since a bodily contact between the tube furnace and the specimen support likewise only occurs in the vicinity of the flanges, the electrical and thermal resistance are so large that current and heat flow between tube furnace and specimen support are predominantly excluded and the heating of the specimen substance takes place practically exclusively by irradiation. The flanges disposed symmetrically with respect to the tube ends additionally delimit a central part of the furnace in which approximately isothermal conditions prevail. Such conditions also guarantee reproducible results when atomization of the specimen substance takes place at the tube wall of the furnace.

A configuration being formed of a graphite tube furnace and a specimen support with a radially symmetrical flange disposed in the interior of the tube is known from German Published, Non-Prosecuted Application DE-OS No. 37 22 379 A1. That flange is provided with grooves through which the holder part of the specimen support is slid. If too small a clearance is provided, such as when fixing the specimen support in slots at the end, the tube can rupture as a consequence of differential thermal expansion of both parts. However, different expansions, which can hardly be avoided with the usual range of graphite products, does not affect the functioning of a graphite furnace in which the specimen support lies freely on flanges and which must be correspondingly provided at least as a pair.

Tube furnaces and specimen supports are formed of any desired type of graphite, such as electrographite, pyrographite or vitreous carbon. The purest graphite obtained from electrographite, which is easily workable and only slightly rendered impure by foreign elements, is preferred. Tube furnaces and supports are advantageously coated with a thin pyrographite layer which seals the graphite parts and improves the abrasion resistance thereof.

Other features which are considered as characteristic for the invention are set forth in the appended claims.

Although the invention is illustrated and described herein as embodied in a graphite tube furnace with a specimen support for atomic absorption spectroscopy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 2 is a fragmentary, longitudinal-sectional view taken along the line II—II of FIGS. 1 and 3, in the direction of the arrows;

FIG. 3 is a fragmentary, longitudinal-sectional view taken along the line III—III of FIGS. 1 and 2, in the direction of the arrows.

Figure 1:
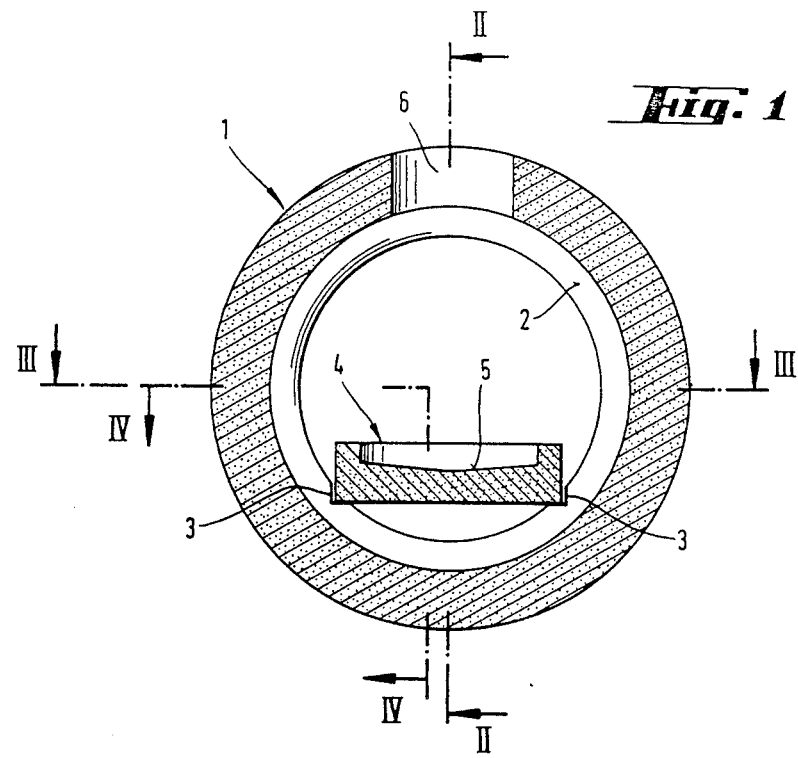
FIG. 1 is a diagrammatic, cross-sectional view of a graphite tube furnace with a specimen support inserted, taken along the line I—I of FIG. 2, in the direction of the arrows.
Figure 4:
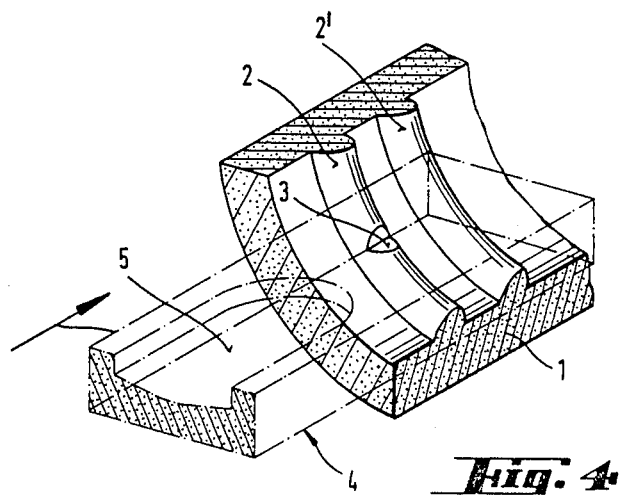
FIG. 4 is a sectional view taken along the line IV—IV in FIGS. 1 and 3, in the direction of the arrows.

Referring now in detail to all of the figures of the drawing as a whole, there is seen a graphite tube furnace 1 provided with circular flanges, ribs or webs 2 in which slot-shaped grooves 3 are formed and an opening 6 for supplying a specimen. A specimen support 4, which is provided with a recess 5 for receiving analysis specimens and with prong-shaped extensions 7, rests on the flanges 2 and is guided in the slot-like grooves 3. An unslotted flange 2' acts like a buffer and limits movement of the specimen support 4, which is engaged in the slot-shaped grooves 3, in a direction parallel to the longitudinal direction or extent of the graphite tube furnace 1.

The size of the support surfaces of the specimen support 4 is determined by the width of the flanges 2 and the depth of the slot-shaped grooves 3. A knife-edged shaped formation of the flanges in particular provides for almost pointlike supports and correspondingly the energy flow through the supports during operation of the furnace is so small that the temperature and temperature distribution of the specimen support are not influenced.

The foregoing is a description corresponding in substance to German Application No. P 38 23 346.0, dated July 9, 1988, the International priority of which is being claimed for the instant application, and which is hereby made part of this application. Any material discrepancies between the foregoing specification and the aforementioned corresponding German application are to be resolved in favor of the latter.

We claim:

1. Graphite tube furnace assembly, comprising a graphite tube furnace having an inner wall surface, at least two peripheral flanges disposed on said inner wall surface, and a specimen support for atomic absorption spectroscopy supported on said flanges in said graphite tube furnace at a distance from said inner wall surface.

2. Graphite tube furnace according to claim 1, wherein said flanges are in the shape of knife edges.

3. Graphite tube furnace according to claim 2, wherein said knife edges have a base width of between 0.5 and 1.0 mm.

4. Graphite tube furnace according to claim 1, wherein said flanges have slot-shaped recesses formed therein for guiding said specimen support.

5. Graphite tube furnace according to claim 1, wherein some of said flanges have slot-shaped recesses formed therein for guiding said specimen support and one of said flanges is free of recesses and limits lengthwise movements of said specimen support like a buffer.

6. Graphite tube furnace according to claim 1, including a pyrocarbon coating disposed on said inner wall surface of said graphite tube furnace.

* * * * *